Figure 1:
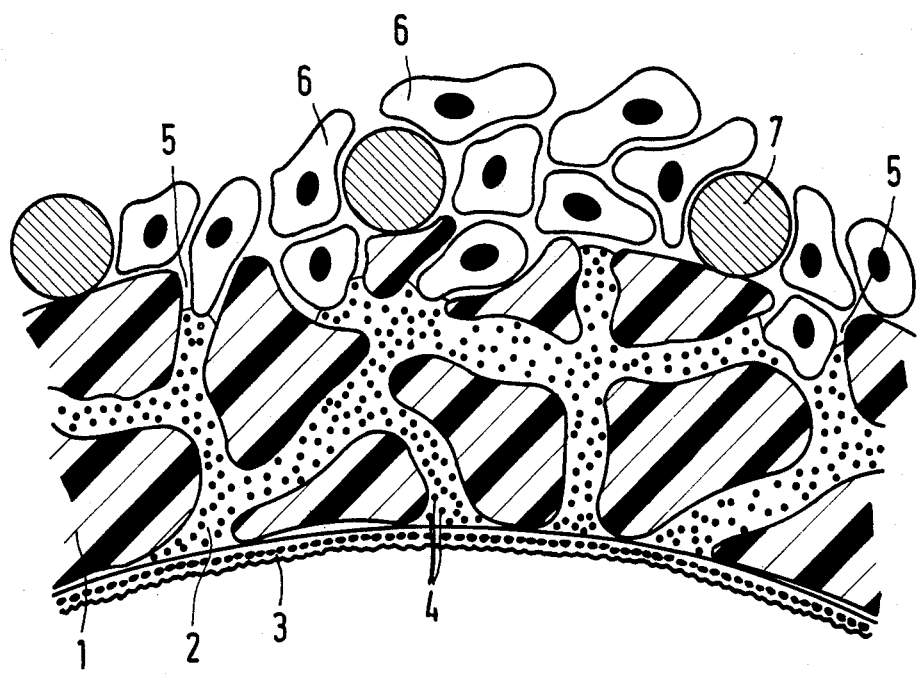

United States Patent [19]

Turina et al.

[11] Patent Number: 4,804,381
[45] Date of Patent: Feb. 14, 1989

[54] ARTIFICIAL VESSEL

[75] Inventors: Marko Turina, Zurich; Peter Bittmann, Herrliberg, both of Switzerland

[73] Assignee: Sulzer Brothers Limited, Winterthur, Switzerland

[21] Appl. No.: 52,243

[22] Filed: May 19, 1987

[30] Foreign Application Priority Data

Jun. 2, 1986 [CH] Switzerland .................. 2219/86

[51] Int. Cl.$^4$ .............................................. A61F 2/06
[52] U.S. Cl. ........................................ 623/1; 623/11; 623/66; 435/240.2
[58] Field of Search .................. 427/2; 428/304.4; 435/174, 180, 182, 240; 623/1, 11, 12, 66

[56] References Cited

U.S. PATENT DOCUMENTS

| | | | |
|---|---|---|---|
| 3,551,560 | 12/1970 | Thiele | 623/1 |
| 4,167,045 | 9/1979 | Sawyer | 623/1 |
| 4,355,426 | 10/1982 | MacGregor | 623/1 |
| 4,377,160 | 3/1983 | Romaine | 128/156 |
| 4,546,500 | 10/1985 | Bell | 623/1 |

FOREIGN PATENT DOCUMENTS 3422639 12/1985 Fed. Rep. of Germany .......... 623/1

Primary Examiner—Richard J. Apley
Assistant Examiner—Paul Prebilic
Attorney, Agent, or Firm—Kenyon & Kenyon

[57] ABSTRACT

The arterial vessel is made of a microporous membrane having pores which are filled with a permeable gel or which are closed over by a thin porous layer. A monolayer of endothelial cells is provided on the internal surface for exposure to the blood flow and smooth muscle cells are layered on the outer surface for increasing the viability of the live cells on the membrane and to impart elasticity. A support structure formed of a braided construction of monofilaments of inert material can be provided to limit dilation of the vessel.

18 Claims, 1 Drawing Sheet

ARTIFICIAL VESSEL

This invention relates to an artificial vessel. More particularly, this invention relates to an artificial vessel wall for arterial vessels having an inner diameter of less than seven millimeters.

Heretofore, it has been known to provide arterial substitutes for vessels. Further, experience has taught that substances which are impermeable to fluids and especially to water, nutrients, tissue fluid and metabolic products are not suitable as artificial vessel walls. This is because the movements of the tissue fluids through the vessel walls are largely hindered. This, in turn, leads to disturbances in the physiological equilibrium as well as to severe body reactions. Thus, the artificual vessel walls must have at least some permeability to fluids.

The problem of providing arterial substitutes for large vessels, for example, in the area between the aorta and the groin area has been largely solved through the use of textile prostheses and the use of expanded polytetrafluoroethylene prostheses. In these relatively large vessels, the permeability of the vessel wall is achieved through the textile structure or through a stretch-distend process with the tissue growing in simultaneously from outside to provide a simultaneous fixation.

However, in the case of small artificial vessels, for example, of the kind having a small lumen with an inner diameter below seven millimeters, there is an inclination to occlusion. In this respect, the interaction between blood and synthetic material leads to the formation of a fibrin layer with narrowing of the lumen as a consequence. This, in turn, causes the velocity of the blood flow to decrease and further favors depositions and thrombosis development of the prosthesis. In order to address this difficulty, it has been known from German Pat. No. 3422639 to provide glandula prostheses in which the inside of the vessel is lined before implantation with a gap-less monolayer of the patient's own endothelial cells.

It is also known that fluid-permeable gel substances, for example, aqueous gels of an agar agar or polyacrylamide base have sufficient permeability. However, such gel substances are unsuitable for use as a vessel wall since the substances do not have sufficient mechanical strength, for example, to withstand the pressure pulsations of an arterial blood stream.

Accordingly, it is an object of the invention to provide an artificial vessel having a lumen of less than seven millimeters.

It is another object of the invention to provide a mechanically stable vessel for vessels of small lumen.

It is another object of the invention to provide a permeable vessel wall on which the formation, adhesion and viability of a monolayered lining of endothelial cells is ensured.

It is another object of the invention to reduce the risk of occlusion in artificial vessels of relatively small lumen.

Briefly, the invention provides an artificial vessel which is comprised of a porous membrane of bio-inert synthetic material having completely open micropores, a means for smoothing an internal surface of the membrane while at least partially maintaining the permeability of the membrane and a closed monolayer of endothelial cells on the internal surface of the membrane.

The porous membrane may be made of a polyurethane of a thickness of from 0.1 to 1 millimeters. In addition, the micropores of the membrane have a diameter at least partially between 10 and 50 $\mu$m, and preferably a diameter of 30 $\mu$m.

The means of smoothing the internal surface of the membrane may be in the form of an aqueous gel which fills the micro pores and which is permeable, for example, to molecules of a molecular weight up to 100,000 Dalton. Alternatively, the means of smoothing the internal surface of the membrane may be in the form of a porous layer having pores of a diameter at least approximately comparable to the dimensions of the endothelial cells.

The artificial vessel may also be provided with a support structure about the membrane for limiting dilation of the membrane. In this respect, the support structure may consist of a knitted textile having a stitch width of from 0.2 to 2 millimeters.

The use of a membrane of synthetic material provides the necessary mechanical stability required of the vessel with the permeability of the membrane being ensured through the completely open micropores. To this end, the size of the pores between 10 and 50 $\mu$m and preferably 30 $\mu$m is such as to permit a simultaneous fixation of the vessel through tissue growing in from the outside or growing on the outside.

In order for adhesion and viability of a monolayer of endothelial cells to be achieved, it is necessary that the endothelial cells form a closed continuous lining. Their adhesion on the synthetic material on which they grow, forming a basal membrane of type IV collagen, must be so great that they are not torn away with the blood stream. When using membranes of synthetic material, the pore sizes of which lie in the range mentioned, it has been shown that endothelial cells cannot grow over such large "holes" in the surface of the synthetic material, so that a closed layer of endothelial cells does not form. By "smoothing" the surface of the membrane at least on the inside, that is, by filling or covering the "large" pores prepared in this way, the endothelial cells can grow over these distruptive sites so as to form a closed continuous monolayer.

In order to increase the viability of live cells on the membrane, the outer surface of the membrane, is layered with cells of smooth, elastic fiber-producing muscle (SMC: smooth muscle cells). This permits interactions of a biochemical and physiological nature to occur between the endothelial cells and the muscle cells, which can be mono- or multi-layered. The elastic fibers produced by the muscle cells further reinforce the membrane of the vessel wall and ensure elasticity even if the synthetic material of the membrane experiences potential long term changes.

As is well known, natural vessel walls are formed in such a way that with increasing internal pressure they show an elastic dilation, which moves toward an upper limit as the pressure increases. Membranes of synthetic material posses these properties only to an imperfect degree. The support structure which is provided permits the membrane to expand in a controlled manner. In this connection, a support structure of braided material of individual spirally arranged monofilaments of polyester threads of 10 to 40 $\mu$m diameter has particularly proven itself. The braiding, the individual filaments of which are practically inelastic, achieves a certain amount of elasticity by means of the textile structure, in that the individual filaments arrange themselves around each other in response to pressure changes. Experimental tests have shown in this connection that the linear extensibility of the artificial vessel wall can be 0.03 to 0.1% per mm Hg pressure increase in a pressure range of the internal pressure of 80 to 150 mm Hg. The spiral structure of the braiding has a high degree of resistance to kinking and thus lends an increased buckling stability to the membrane.

Figure 2:
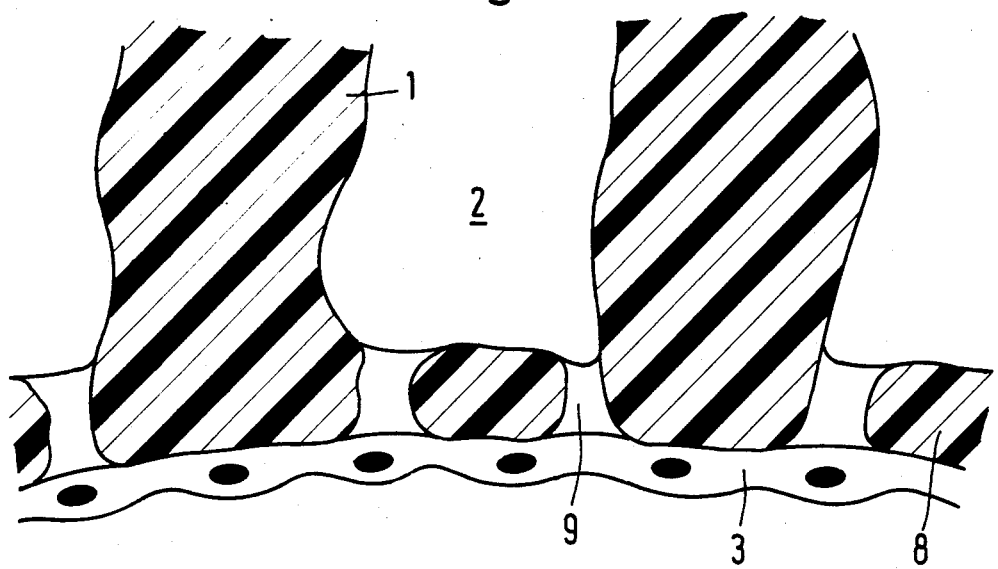

These and other objects and advantages of the invention will become more apparent from the following detailed description taken in conjunction with the accompanying drawings wherein:

FIG. 1 schematically illustrates to an enlarged scale a cross-section through a vessel wall constructed in accordance with the invention; and FIG. 2 Illustrates an enlarged view of a modified vessel wall constructed in accordance with the invention.

Referring to FIG. 1, the artificial vessel is constructed for particular use with small lumens and particularly lumen having an internal diameter of seven millimeters and less. As indicated, the vessel includes a porous membrane 1 of bio-inert synthetic material having completely open micropores 2. Preferably, the membrane 1 is made of a polyurethane with a thickness between 0.2 and 1 millimeter. The micropores 2 form a network and have diameters which are predominantly between 10 and 50 µm. As shown, the micropores 2 are open to the outer surface as well as to the internal surface of the membrane 1.

In addition, the vessel has a closed monolayer 3 of live endothelial cells on the internal surface of the membrane 1. Since these cells either cannot or with only great difficulty grow over the micropores 2 since the diameters of the micropores 2 are a multiple of the dimensions of the cells 3, the vessel is provided with a means for smoothing the internal surface of the membrane 1 while at least partially maintaining the permeability of the membrane. To this end, the means for smoothing is in the form of an aqueous gel 4 which fills the micropores 2.

The gel 4 may be, for example, a 6% agarose or a 12 to 18% of polyacrylamide gel which fills the micropores 2 in accordance with a known immersion process. After immersion, the gel can be partially removed from the outer surface of the membrane 1 in order to create hollow spaces 5 into which cells 6 may grow, for example, for fixation of the artificial vessel in a human body.

The cells 6 consist of smooth muscle cells 6 (SMC), which are cultured in a well known manner and applied in mono- or multi-layered manner on the membrane or outer vessel wall. These smooth muscle cells 6 serve to increase the "compatibility" of the artificial vessels in the body through physiological and biochemical interactions through the membrane 1. The cells 6 also produce elastic muscle fibers which increase the mechanical stability of the artificial vessel. These interactions are made possible not only through the permeability but also through the elasticity of the synthetic membrane 1, which transmits the pressure pulses of the blood stream to the muscle cells 6 and stimulates their production of elastic fibers (elastin).

As already mentioned, the dilatability of natural vessels and that of endothelial cells is limited. In order to achieve a similar limitation, a support structure is provided about the membrane 1. This support structure includes individual threads 7 which are distributed over the outer surface of the membrane 1. These threads 7 are, for example, inelastic monofilaments of polyester with a diameter of 10 to 40 µm.

For an artificial artery-like vessel, the support structure of threads 7 is peripherally closed and consists, for example, of braiding, the monofilaments of which run spirally. The structure has a limited elasticity because of the ability of the individual threads 7 to shift mechanically. The thickness of the threads 7 and a stitch width of the braiding of, for example, 0.2 to 2 mm permit a limitation of the linear dilation at an internal pressure in the physiological range between 80 to 150 mm Hg of from 0.03 to 0.1% per mm Hg pressure increase.

The membrane 1 can be produced, for example, by the known process of phase separation at low temperature.

The gel 4 can be prepared using different known procedural steps combined with each other. Further, an agarose gel may also be conditioned in a known manner through electrical surface charges to improve the ability of live cells to grow into the membrane 1.

Sterilization of the vessel to be implanted and of the individual parts may take place, for example, by chemical means through immersion in a sterilizing solution.

Referring to FIG. 2, wherein like reference characters indicate like parts as above, the means for smoothing the internal surface of the membrane 1 may be in the form of a thin porous layer 8, the thickness of which is from one-tenth to one-hundreth of the thickness of the membrane 1. Of advantage, the porous layer 8 may be formed of the same basic material as the membrane 1. In addition, the porous layer 8 has pores 9 of a diameter at least approximately comparable to the dimensions of the endothelial cells 3, which is several micrometers, for example 3 to 10 µm. The porous layer 8 thus serves to close the internal surface of the membrane 1 which is in contact with the blood stream.

The production of the thin layer 8 may utilize any known procedure known in the technology of membranes wherein the pore size grows specifically in one direction with the aid of the known procedures of phase separation or phase inversion as is known from ultrafiltration techniques.

The invention thus provides an artificial vessel for relatively small lumen, for example, those having an internal diameter of seven millimeters and less, which possess a mechanical strength to absorb the pulsations of a blood flow while at the same time not creating conditions which might lead to occlusions.

What is claimed is:

1. An artificial vessel comprising
   a porous membrane of bio-inert synthetic material having completely open micropores;
   a permeable aqueous gel filling said micropores; and
   a closed monolayer of endothelial cells on an internal surface of said membrane.

2. An artificial vessel as set forth in claim 1 wherein at least some of said micropores have a diameter between 10 and 50 µm.

3. An artificial vessel as set forth in claim 1 which further comprises a layer of smooth elastic fiber-producing muscle cells on an external surface of said membrane.

4. An artificial vessel as set forth in claim 3 wherein said membrane is tubular and which further comprises a support structure about said membrane for limiting dilation of said membrane.

5. An artificial vessel comprising
   a porous tubular membrane of bio-inert synthetic material having completely open micropores;

a porous layer on an internal surface of said membrane and having a plurality of pores therein; and
a closed monolayer of endothelial cells on said layer, said pores of said layer having a size approximately equal to one of said endothelial cells.

6. An artificial vessel as set forth in claim 5 wherein at least some of said micropores have a diameter between 10 and 50 μm.

7. An artificial vessel as set forth in claim 5 which further comprises a layer of smooth elastic fiber-producing muscle cells on an external surface of said membrane.

8. An artificial vessel as set forth in claim 7 which further comprises a support structure about said membrane for limiting dilation of said membrane.

9. An artificial vessel comprising
a porous membrane of bio-inert synthetic material having completely open micropores;
means for smoothing an internal surface of said membrane while at least partially maintaining the permeability of said membrane;
a closed monolayer of endothelial cells on said internal surface of said membrane; and
a layer of smooth elastic fiber-producing muscle cells on an external surface of said membrane.

10. An artificial vessel comprising
a porous membrane of bio-inert synthetic material made of polyurethane of a thickness of from 0.1 to 1 millimeters and having completely open micropores;
means for smoothing an internal surface of said membrane while at least partially maintaining the permeability of said membrane; and
a closed monolayer of endothelial cells on said internal surface of said membrane.

11. An artificial vessel comprising
a porous membrane of bio-inert synthetic material having completely open micropores;
an aqueous gel filling said micropores and being permeable to molecules of a molecular weight up to 100,000 Dalton to smooth an internal surface of said membrane while at least partially maintaining the permeability of said membrane; and
a closed monolayer of endothelial cells on said internal surface of said membrane.

12. An artificial vessel comprising
a porous membrane of bio-inert synthetic material having completely open micropores;
a porous layer for smoothing an internal surface of said membrane while at least partially maintaining the permeability of said membrane; and
a closed monolayer of endothelial cells on said porous layer with said porous layer having pores of a diameter equal to the dimensions of an endothelial cell.

13. An artificial vessel comprising
a porous tubular membrane of bio-inert synthetic material having completely open micropores;
means for smoothing an internal surface of said membrane while at least partially maintaining the permeability of said membrane;
a closed monolayer of endothelial cells on said internal surface of said membrane, and
a braided support structure about said membrane for limiting dilation of said membrane.

14. An artificial vessel comprising
a porous membrane of bio-inert synthetic material having completely open micropores, at least some of said micorpores having a diameter between 10 and 50 μm;
means for smoothing an internal surface of said membrane while at least partially maintaining the permeability of said membrane; and
a closed monolayer of endothelial cells on said internal surface of said membrane.

15. An artificial vessel as set forth in claim 14 wherein said micropores have a diameter of 30 μm.

16. An artificial vessel as set forth in claim 13 wherein said support structure consists of a knitted textile having a stitch width of from 0.2 to 2 millimeters.

17. An artificial vessel as set forth in claim 16 wherein said membrane has a linear elasticity of from 0.03 to 0.1% per mm Hg pressure increase at an internal pressure of 80 to 150 mm Hg.

18. An artificial vessel as set forth in claim 16 wherein said braided support structure consists of a braiding of individual spirally arranged filaments of polyester threads of 10 to 40 μm diameter.

* * * * *

UNITED STATES PATENT AND TRADEMARK OFFICE
CERTIFICATE OF CORRECTION

PATENT NO. : 4,804,381

DATED : February 14, 1989

INVENTOR(S) : MARKO TURINA, et al

It is certified that error appears in the above-identified patent and that said Letters Patent is hereby corrected as shown below:

Column 6, line 26 change "micorpores" to -micropores-

Signed and Sealed this

Thirtieth Day of April, 1991

Attest:

HARRY F. MANBECK, JR.

Attesting Officer

Commissioner of Patents and Trademarks